United States Patent
Moigne (12)

(10) Patent No.: US 6,346,252 B1
(45) Date of Patent: Feb. 12, 2002

(54) METHOD OF OBTAINING AN ANTIBACTERIAL AND/OR ANTIFUNGAL EXTRACT FROM THE ALGAE, BONNEMAISONIACEA

(75) Inventor: Jean-Yves Moigne, Kerinec (FR)

(73) Assignee: Algues et Mer (S.A.R.L.), Kernigou (FR)

( * ) Notice: Subject to any disclaimer, the term of this patent is extended or adjusted under 35 U.S.C. 154(b) by 0 days.

(21) Appl. No.: 09/242,756

(22) PCT Filed: Sep. 11, 1997

(86) PCT No.: PCT/FR97/01603

§ 371 Date: Nov. 18, 1999

§ 102(e) Date: Nov. 18, 1999

(87) PCT Pub. No.: WO98/10656

PCT Pub. Date: Mar. 19, 1998

(30) Foreign Application Priority Data

Sep. 12, 1996 (FR) .............................. 96 11149

(51) Int. Cl.[7] .............................. A61K 35/80
(52) U.S. Cl. .............. 424/195.17; 424/401; 424/78.02; 424/78.03; 424/78.07; 514/881; 514/944
(58) Field of Search .............. 424/401, 78.02, 424/78.03, 78.05, 78.07, 195.17; 514/881, 944

(56) References Cited

U.S. PATENT DOCUMENTS 4,897,266 A    1/1990    Herve

FOREIGN PATENT DOCUMENTS

WO    84/02652    7/1984

OTHER PUBLICATIONS

Biological Abstracts, vol. 90, abstract No. 312461, XP002032483, J. Natl Sci Counc Sri Lanka, vol. 16, No. 2, pp 209–222, 1988.

Biological Abstracts, vol. 82, abstract No. 159831, XP002032484, Plant Med O (Suppl), pp 152–162, 1980.

Biological Abstracts, vol. 80, abstract No. 153462, XP002032485. Bot. Mar. vol. 22, No. 7, pp 451–454, 1979.

Biological Abstracts, vol. 95, abstract No. 489453, XP002032486, Microbios vol. 83, No. 334, pp 23–26, 1995.

Halogen Chemistry of the red Alga Asparagopsis, McConnell et al., vol. 16, pp 367–374 XP002032482, 1977.

Database WPI, Derwent Publications LTD., London, GB; AN 95–011755, XP002032488.

*Primary Examiner*—Raj Bawa
(74) *Attorney, Agent, or Firm*—Wolf, Greenfield and Sacks, P.C.

(57) ABSTRACT

A clarified algae extract used to obtain a composition having antibacterial and/or antifungal activity, said extract being obtained according to a method comprising the stages of release of the intracellular content of the algae cells and clarification by filtration of said intracellular content, in order to obtain a clarified filtration permeate, said extract comprising a molecular fraction containing halogenated organic molecules having a molecular weight of more than 10,000.

7 Claims, No Drawings

METHOD OF OBTAINING AN ANTIBACTERIAL AND/OR ANTIFUNGAL EXTRACT FROM THE ALGAE, BONNEMAISONIACEA

RELATED APPLICATIONS

This application claims foreign priority benefits under Title 35, U.S.C., §371 of PCT application no. PCT/FR97/01603, filed Sep. 11, 1997, and foreign patent application no. FR 96 11149, filed Sep. 12, 1996, the entire contents of which are incorporated herein by reference.

GOVERNMENT SUPPORT

Not applicable.

FIELD OF THE INVENTION

The invention relates to an algae extract comprising halogenated organic compounds, and to use of this extract as an antibacterial, bacteriostatic or bactericidal, and/or antifungal, fungistatic or fungicidal agent.

BACKGROUND

Some algae are known to have antibacterial or antifungal action. These are the Rhodophycea in particular, but also include Chlorophycea and Pheophycea. Among the Rhodophycea, the algae belonging to the Bonnemaisoniacea, in particular the algae of the Asparagopsis species, are known to have remarkable antibacterial and antifungal action. In this respect, reference can be made to the document entitled "Fixed algae of the French Atlantic Coast containing antibacterial and antifungal substances" (J. F. Biard et al, Planta medica, Journal of Medicinal Plant Research, 1980, supplement, pages 136–151).

*Asparagopsis Armata* is a sea alga that is most often epiphyte which originally came from Australia or New Zealand. This alga has existed in the Northern hemisphere since the 1920's and it can be found in England, Ireland, France, Spain, Italy and Morocco where it nevertheless grows in very scattered, unstable populations to depths of up to ten metres. It is one of the reasons why industrial use of the halogenated organic compounds that these algae contain, hand-picked in their natural habitat, has not been considered.

A further reason is given in an article entitled "Halogen chemistry of the red alga Asparagopsis" (Olivier McConnell and Willliam Fenical, Phytochemistry, 1977, vol. 16, pages 367–374). The halogenated organic compounds of the algae which, according to the article's authors, account for their antibacterial and antifungal action, comprise 1 to 4 carbon atoms and are very volatile. This is why the authors only describe one complex method for extracting these compounds, a laboratory-conducted method, in which the volatile molecules are expelled in a stream of hot air, followed by multi-solvent, controlled extraction.

SUMMARY

The applicant, however, has developed a culture technique using microcuttings, described in French patent application n° 95 03577 filed on Mar. 22, 1995. With this technique, it is possible to obtain a substantial quantity of Asparagopsis algae in a short time which can be used at industrial level.

Having regard to the above, one problem which the invention sets out to solve is to obtain a clarified extract of algae by means of a method which may be applied at industrial level using a substantial quantity of algae, and to use such method to obtain a composition having antibacterial and/or antifungal activity.

One solution to this problem consists of conducting a clarification operation by filtering the intracellular content of the algae, such as to obtain a permeate having a molecular fraction containing molecules with a molecular weight of more than 10000, said fraction being, at least in part, responsible for the antibacterial or antifungal action.

Therefore, the object of the invention is use of a clarified algae extract to obtain a composition having antibacterial and/or antifungal activity, said extract being obtained in accordance with a method comprising the stages of release of the intracellular content of the algae cells and clarification by filtering of said intracellular content with a view to obtaining a clarified filtration permeate, said extract comprising a molecular fraction containing halogenated organic molecules having a molecular weight of more than 10000.

Also, said extract may be used to obtain a cosmetic and/or pharmaceutical composition.

BRIEF DESCRIPTION OF THE DRAWINGS

Not applicable.

DETAILED DESCRIPTION

The description given below is in no way restrictive. It is written in relation to the example of the red alga (Rhodophycea) *Asparagopsis Armata* which belongs to the Bonnemaisoniacea family. Needless to say, the invention extends to all algae species comprising halogenated intracellular organic compounds.

*Asparagopsis Armata* is a multicell alga of which some cells, or vesicles of these cells, comprise a great quantity of halogenated compounds, especially brominated and iodinated compounds.

Among the halogenated organic compounds of *Armata Asparagopsis*, mention may be made of the following compounds, the molecular weights of said compounds being given in brackets:

halomethanes: $CHBr_3$ (253), $CH_3I$ (142), $CH_2ClI$ (176), $CHCl_3$ (119), $CCl_4$ (152), $CHBrCl_2$ (163), $CHBr_2Cl$ (208), $CBr_4$ (332), $CHBr_2I$ (220);

haloacetones: $CH_2Br$—CO—$CH_2Cl$ (171), $CH_2Br$—CO—$CH_2Br$ (216), $CHBr_2$—CO—$CH_2Cl$ (250), $CHBrCl$—CO—$CH_2Br$ (250), $CHBr_2$—CO—$CH_2Br$ (295), $CHBr_2$—CO—$CHBrCl$ (329), $CHBr_2$—CO—$CHBr_2$ (374), $CH_2Br$—CO—$CH_3$ (137), $CHBr_2$—CO—$CH_3$ (216), $CHCl_2$—CO—$CHBrCl$ (229), $CHBr_2$—CO—$CHCl_2$ (285), $CHBrCl$—CO—$CHBrCl$ (284), $CHCl_2$—CO—$CHCl_2$ (196);

haloisopropanols: $CHBr_2$—CHOH—$CH_2Br$ (297), $CHBr_2$—CHOH—$CHBr_2$ (373);

haloacetates: $CH_2I$—COO—$CH_3$ (200), $CHBr_2$—COO—$CH_3$ (232), $CHBr_2$—COO—$C_2H_5$ (246), $CHBrI$—COO—$C_2H_5$ (283); and halogenated acrylic acids: $CBr_2$=CH—COOH (230) $CBr_2$=CH—COO—$CH_3$ (244),$CHBr$=CH—COO—$C_2H_5$ (169), $CHBr$=CI—COO—$C_2H_5$ (292).

It will be noted, however, that other halogenated organic compounds have been reported in algae belonging to the same family. These compounds are present in said algae in varying quantities depending upon species, and even vary within one same species between different harvested batches.

To obtain the extract of the invention, *Asparagopsis Armata* was cultivated and harvested using a method such as described in above-mentioned French application n° 95 03577 filed on Mar. 22, 1995, whose content is incorporated into the present invention for reference purposes.

The fresh harvested alga is packed and sealed in vacuum packs.

These packs are frozen to a temperature of less than 0° C., in practice in the region of −18° C. At this temperature, the free water in the algae cells and in the vesicles contained in these cells, crystallizes. Since the temperature is lowered gradually to reach the freezing temperature, the crystals formed are voluminous and cause initial bursting of the algae cells.

The above-mentioned packing and freezing stages are advantageously conducted as soon as possible after harvesting. In this way, losses of volatile organo-halogenated compounds are restricted.

The packed, frozen algae can be preserved and stored frozen for a relatively long period, in practice for several years.

If it is wished to obtain an extract of the invention, the frozen algae are first crushed in order to obtain advanced cell bursting through the shearing effect of the ice crystals,. This crushing operation is stopped as soon as the temperature reaches 0° C.

Over and above 0° C., the algae mature inside their packs. Enzymes of the algae cause degradation of the carragheens (depolymerisation) and other gelling compounds contained in the algae, and the intracellular matter of the algae cells liquefies.

This is the reason why maturing at low temperature, 4° C. maximum, is subsequently conducted for a time period t, for example 200 hours, in order to obtain natural enzymatic degradation of the polysaccharides with no loss of the activity that is the subject of the invention.

Subsequently, extremely fine grinding of the matured algae is carried out, such that the cells and vesicles of said algae burst and grindings are obtained in which the intracellular and intravesicular content of the algae has been released.

This last grinding stage, and the subsequent stages for obtaining the extract of the invention, are conducted at a controlled temperature of less than 10° C., preferably in the region of 4° C.

It is preferable to adjust the quantity of dry matter of the grindings to a value of no more than 8% by weight. In practice, the quantity of dry matter in said grindings is in the region of 10 to 11% by weight. Therefore, 30% of water is added. The extraction yield of the cell content is consequently optimized.

The grindings are then centrifuged, for example on Jouan KR 4-22 equipment at 4500 for 15 min. A residual part and a supernatant are obtained. The residual part, essentially made up of a solid phase, comprises the membrane walls of the algae cells. The supernatant, which contains the intracellular matrix and, hence the halogenated organic compounds, is collected.

This supernatant, whose pH is approximately 5.94, is preferably acidified with citric acid to a value of between 2 and 5, for example 3.35.

It is then clarified by filtering. For this purpose, tangential microfiltration of said supernatant is preferably used. The clarification threshold is in the region of 1.5 μm. Over and above this value, clarification does not take place. Below this value, the compounds responsible for the activity of the extract of the invention are filtered, and virtually all the activity initially present in the supernatant is collected using a value in the region of 1.4 μm, which more or less corresponds to the clarification threshold.

With this microfiltration stage, and with no prior stages of drying or solubilizing in solvents and evaporation, a limpid, liquid, clarified algae extract of the invention is obtained, which is slightly yellowish in colour.

Tests were conducted with this extract for the purpose of assessing its antibacterial and antifungal properties on different bacterial strains, yeasts or moulds. The results of these tests are given in the following table, in which the population decrease at 20 or 32° C. and at 5, 30 or 60 minutes was measured for each bacterial strain,. It will be noted that a reduction of $10^5$ relates to a so-called 5 log decrease as is required by standards in force.

| | 20° C. 5 min | 20° C. 30 min | 20° C. 60 min | 32° C. 5 min | 32° C. 30 min | 32° C. 60 min |
|---|---|---|---|---|---|---|
| *Vibrio Anguillarum* | $>10^5$ | $>10^5$ | $>10^5$ | $>10^5$ | $>10^5$ | $>10^5$ |
| *Pseudomonas Aerinosa* | }10; $10^3$} | }$10^3$; $10^5$} | $>10^5$ | }$10^3$; $10^5$} | $>10^5$ | $>10^5$ |
| *Escherichia Coli* | | }10; $10^3$} | }10; $10^3$} | | | $>10^5$ |
| *Enterobacter Gergoviae* | | | }10; $10^3$} | | | $>10^5$ |
| *Staphylococcus aureus* | | | }$10^3$; $10^5$} | | | $>10^5$ |
| *Candida Albicans* | | | }$10^3$; $10^5$} | | | $>10^5$ |

As is shown by this table, the antibacterial activity of the extract is proven on the bacterial strains *Vibrio anguillarum, Pseudomonas aeruginosa, Escherichia coli, Enterobacter gergoviae, Staphylococcus aureus*, and antifungal activity on the *Candida albicans* strain with an optimum contact time of 60 minutes maximum.

Analysis of the extract of the invention shows that it contains 2.03% by weight of dry matter obtained at 120° C., 21.2% by weight of said dry matter, calculated at 550° C., being made up of organic matter. Analysis of the composition of this dry matter gave the following results expressed in g/kg of dry matter:

| | |
|---|---|
| Proteins | 68.9 |
| Reducing sugars | 53.7 |
| Mannitol | 63.0 |
| Sodium | 256 |
| Potassium | 30.5 |
| Calcium | 12.8 |
| Magnesium | 13.2 |
| Lead | 0.50 |
| Cadmium | 0.25 |
| Zinc | 38.5 |
| Arsenic | 6.0 |
| Copper | 6.0 |
| Mercury | <0.25 |
| Selenium | <2.5 |
| Sulphur ($SO_4$) | 55.1 |

In addition, titration of the halogens (iodine, chlorine, bromine) present in the extract gave the following results, again expressed in g/kg of dry matter:

| | |
|---|---:|
| Total iodine (inorganic and organic) | 8.4 |
| Chlorides | 426 |
| Total bromine (inorganic and organic) | 120.5 |

It is to be noted that the above results, and most of the results given below, are related to the batches of algae tested. However, a coherence does exist between the results obtained, irrespective of batches.

For additional analysis, a sample of 33 ml of extract of the invention, extracted in 4 ml of hexane, gave the following results expressed in mg/l:

| | |
|---|---:|
| $CHBr_2Cl$ | 0.36 |
| $CHBr_3$ | 39.4 |
| $CH_2I_2$ | 0.12 |
| $ChBr_2I$ | 8.4 |
| $CHBrI_2$ | 0.4 |
| $CHI_3$ | 0.3 |

It therefore appears that, in the extract of the invention, $CHBr_3$ bromoform is largely in majority, even if dibromo-iodo-methane is present in substantial quantity. At a much lower level, other halogenated micromolecules are found.

In order to test that the antibacterial and/or antifungal action is in fact related to a group of halogenated molecules of low molecular weight, an aqueous solution of 60 mg/l bromoform was prepared and its action compared with that of a permeate of nanofiltration at the threshold of 400 Daltons which therefore only contained micromolecules, in particular halogenated molecules. After embedding 1 ml and 0.1 ml samples in a PCA medium for 48 hours from a mother solution containing the product to be tested and the *Pseudomonas aeruginosa* strain at a concentration of 1.9 $10^8$, the results in the following table were obtained.

| T | Embeddings | Bromoform 60 mg/l | Permeate 400 D |
|---|---|---|---|
| 48 hours | 1 ml | >> | 0 |
| | 0.1 ml | >> | $2.0\ 10^2$ |

In this table, and in the following tables, ">>" means that bacteria developed and could not be counted.

It would therefore appear that the bromoform alone, at a concentration of 1.5 times that observed in the extract, has no action against the Pseudomonas aeruginosa strain. On the other hand, the 400 D nanofiltration permeate is active against this strain on the second day after its production. It can be deduced therefrom that the action of the 400 D permeate is due to the synergetic action of the halogenated micromolecules even in trace from.

Also, the microfiltration permeate was fractionated by subjecting it to ultrafiltration (uF) or nanofiltration (nF), and the antibacterial action on the Pseudomonas strain was measured for each fraction and at different times in accordance with the protocol described below. The following results were obtained:

| | | Extract | uF Reten. | uF Perm. | nF Reten. | nF Perm. |
|---|---|---|---|---|---|---|
| T = 2 days | 1 ml | 0 | 0 | 0 | 0 | 0 |
| | 0.1 ml | $1.0\ 10^2$ | $2.0\ 10^2$ | $1.4\ 10^3$ | $2.0\ 10^2$ | $2.0\ 10^2$ |
| | m. sol. | $2.0\ 10^8$ | $2.0\ 10^8$ | $2.0\ 10^8$ | $2.0\ 10^8$ | $2.0\ 10^8$ |
| t = 1 month | 1 ml | 0 | 0 | $5.10^1$ | 0 | 0 |
| | 0.1 ml | 0 | 0 | $1.3\ 10^3$ | 0 | 0 |
| | m. sol. | $2.0\ 10^8$ | $2.0\ 10^8$ | $2.0\ 10^8$ | $2.0\ 10^8$ | $2.0\ 10^8$ |
| t = 2 months | 1 ml | 0 | 0 | >> | 0 | >> |
| | 0.1 ml | $1.0\ 10^4$ | 0 | >> | 0 | >> |
| | m. sol. | $1.2\ 10^8$ | $1.2\ 10^8$ | $1.2\ 10^8$ | $1.2\ 10^8$ | $1.2\ 10^8$ |

The ultrafiltration threshold corresponds to molecules of 10000 D and the nanofiltration threshold to molecules of 400 D. From the above, it is found that the permeate fractions of ultrafiltration and nanofiltration quickly lose their activity, in less than 2 months, whereas the retentates preserve their activity. Also, analyses conducted on these batches showed a higher organic iodine concentration in the retentates. It can therefore be deduced that the active properties of the extract could be generated by macromolecules having a molecular weight of more than 10000 whose type is not clearly identified to date. It is probable that these molecules are protein-polysaccharide complexes containing bromine and iodine in particular.

These macromolecules apparently act as a reserve matrix. Natural, perhaps enzymatic, degradation of said macromolecules may lead to the formation of halogenated micromolecules responsible for the activity. This was confirmed by additional tests in which it was shown that the aged extract contains 6 times more bromoform than the non-aged extract and 70 times more dibromo-iodo-methane.

The halogenated macromolecules have a molecular weight of less than 400. Their presence in the ultrafiltration and nanofiltration permeates accounts for the attested action of these fractions for a short period. These macromolecules subsequently degrade into halides, in particular into inorganic iodides and bromides.

Other tests were conducted to measure the influence of pH on the extract's activity and its ageing. Acidification was carried out during the so-called acidification stage of the method for obtaining the extract of the invention, using citric acid. The results of these tests on the Pseudomonas strain are given in the following table:

| | | pH = 3.35 | pH = 4.04 | pH = 5.94 |
|---|---|---|---|---|
| t = 2 days | 1 ml | 0 | 0 | 0 |
| | 0. 1 ml | 0 | 0 | 0 |
| | m. sol. | $2.0\ 10^8$ | $2.0\ 10^8$ | $2.0\ 10^8$ |
| t = 1 month | 1 ml | 0 | 0 | 0 |
| | 0. 1 ml | $2.2\ 10^3$ | 0 | $3.3\ 10^4$ |
| | m. sol. | $2.4\ 10^8$ | $2.5\ 10^8$ | $2.8\ 10^8$ |
| t = 2 months | 1 ml | 0 | 0 | 0 |
| | 0. 1 ml | $1.6\ 10^4$ | $2.7\ 10^4$ | >> |
| | m. sol. | $3.2\ 10^8$ | $2.2\ 10^8$ | $2.2\ 10^8$ |
| t = 3 months | 1 ml | 0 | 0 | 0 |
| | 0. 1 ml | 0 | $2.0\ 10^4$ | >> |
| | m. sol. | $3.0\ 10^8$ | $3.1\ 10^8$ | $3.1\ 10^8$ |
| t = 4 months | 1 ml | 0 | 40 | 0 |
| | 0. 1 ml | $3.0\ 10^4$ | > | >> |
| | m. sol. | $3.5\ 10^8$ | $2.9\ 10^8$ | $2.9\ 10^8$ |
| t = 5 months | 1 ml | 0 | 0 | $1.5\ 10^2$ |
| | 0. 1 ml | 0 | $10^5$ | >> |
| | m. sol. | $1.8\ 10^8$ | $5.0\ 10^8$ | $5.0\ 10^8$ |

-continued

|  |  | pH = 3.35 | pH = 4.04 | pH = 5.94 |
|---|---|---|---|---|
| t = 13 months | 1 ml 0. 1 ml m. sol. | 0 2.10 $10^4$ 3.6 $10^8$ | | |

The activity of the extract of the invention is preserved in an acid medium with an optimum pH value of 3.35. Therefore, acidification at a pH of between 2 and 5, preferably in the region of 3.25, apparently slows down the degradation of the matrix and leads to the slow release of the halogenated active substances. Also, this acidification would seem to stabilize the halogenated micromolecules which accumulate in the medium, and maintain activity for more than 13 months.

According to the invention, the extract is used, in cosmetic and/or pharmaceutical compositions, as a bactericidal or bacteriostatic, or a fungicidal or fungistatic agent. The extract is bactericidal or bacteriostatic, fungicidal or fungistatic according to its concentration in the cosmetic and/or pharmaceutical composition and depending upon the bacterial strains or the yeasts or moulds to which it is applied.

EXAMPLES

The cosmetic compositions below, given by way of example, will give a clearer view of the diversity of cosmetic formulations in which the extract of the invention may be used. In these examples, the trade names of the products used are, whenever applicable, written in brackets, the quantities of product being expressed as a weight percentage.

Example 1
Emulsion-gel

| (Eumulgin B1) | 2.5 |
|---|---|
| Glyceryl stearate (Cutina GMS) | 2.5 |
| Mineral oil (Vaseline) | 4.0 |
| (Lanol wax CTO) | 2.0 |
| Cyclomethicone (Abil K4) | 1.5 |
| Sweet almond oil | 1.5 |
| Carbomer (Carbopol 2001) | 0.5 |
| Triethanolamine | 0.5 |
| Glycerine | 3.0 |
| Alga extract (CLMO2) | 1.0 |
| Extract of the invention | 7.0 |
| (LRI solubilizer) | 0.5 |
| Fragrance | 0.3 |
| Colouring agent | as req. |
| Water | to 100 |

Example 2
Lotion-gel

| (Dermol L-45) | 0.5 |
|---|---|
| Alga extract, propylene glycol, water (CLMO2) | 1.0 |
| Alga extract, propylene glycol, water (FCO2) | 0.5 |
| Sodium PCA, sodium lactate, fructose, collagen | 1.0 |
| Extract of the invention | 7.0 |
| PPG-26 buteth-26, castor oil | 0.5 |

-continued

| Solubilizer LRI | |
|---|---|
| Fragrance | 0.3 |
| Colouring agent | as req. |
| Citric acid | as req. |
| Water | to 100 |

Example 3
Shampoo

| Sodium laureth sulphate (Texapon N70) | 5.0 |
|---|---|
| Sodium laureth sulphate, lauryl polyglucose (Plantaren PS10) | 5.0 |
| Cocoamidopropylbetaine (Dehyton K) | 4.0 |
| Cocoamide DEA, laureth-12 (Comperlan LS) | 1.0 |
| (Glutamate DOE 120) | 0.5 |
| Lauryl methyl gluceth-10 hydroxypropyl dimonium chloride (Glucquat 125) | 0.5 |
| Glycerine | 3.0 |
| Alga extract, propylene glycol, water (CLMO2) | 1.0 |
| Extract of the invention | 7.0 |
| PEG-6 caprilic/capric glycerides (Softigen 767) | 2.0 |
| Fragrance | 0.3 |
| Sodium chloride | 0.2 |
| Colouring agent | as req. |
| Citric acid | as req. |
| Water | to 100 |

In the above compositions, it will be noted that Eumulgin B1 is a polyethylene glycol ether of cetearyl alcohol whose general formula is $R(OCH_2-CH_2)_n OH$ in which R represents a mixture of alkyl groups derived from cethyl and stearyl alcohol and n has an average value of 12; that Lanol CTO wax is made up firstly of a fatty alcohol mixture chiefly containing cethyl and stearyl alcohol, and secondly of a polyethylene glycol ether of cetearyl alcohol whose general formula is $R(OCH_2CH_2)_n OH$ in which R represents a mixture of alkyl groups derived from cethyl and stearyl alcohol and n has an average value of 33; that the solubilizer LRI is a polyoxypropylene, polyoxethylene ether of butyl alcohol having the general formula $C_4H_3(OCH_3CHCH_2)_x(OCH_3CH2)_y OH$ in which x and y have an average value of 26; that Dermol L-45 is an ester of lactic acid comprising a polyethylene glycol ether of glycerine, containing an average of 7 moles of ethylene oxide; that Dehyton K is a zwiterion having the formula $RCONH (CH_2)_3N^+(CH_3)_2CH_2COO^-$ in which RCO represents the fatty acid function derived from coconut oil; that Comperlan LS is a mixture of ethanolamides of coconut acids having the general formula $RCON(CH_2CH_2OH)_2$ in which RC represents the fatty acid function derived from coconut oil and from a polyethylene glycol ether of lauryl alcohol having the formula $CH_3(CH_2)_{10}CH(OCH_2CH_2)_nOH$; that Glucamate DOE120 is a polyethylene glycol ether of the diester of oleic acid and of methyl glucose with 120 moles of ethylene oxide on average; that Glucquat 125 is a quaternary ammonium salt derived from the reaction between a gluceth-10 methyl and a dodecylammonium epoxide dimethyl; and that Softigen 767 is an ethoxyl glyceride having the general formula $RCOOCH_2CHOHCH_2(OCH_2CH_2)_nOH$ in which RCO is a mixture of caprylic or capric radicals and n has an average value of 6.

In addition, tests were conducted in order to determine the efficiency with which a 7% concentration of the extract could protect the basic cosmetic formulas against the later development of aerobic mesophilic germs or yeasts or moulds without the presence of any other preservative. These tests measured the number of germs present at different times, in days, at room temperature or at 45° C. The results obtained are grouped in the following table:

| | | D = 0<br>T = 20° C. | D = 15<br>T = 20° C. | D = 30<br>T = 45° C. |
|---|---|---|---|---|
| Emulsion-gel | Mesophilic aerobic germs | 70 | 10 | <10 |
| | Yeasts | <10 | <10 | <10 |
| | Moulds | <10 | <10 | <10 |
| Lotion-gel | Mesophil aerobic germs | <10 | 10 | <10 |
| | Yeasts | <10 | <10 | <10 |
| | Moulds | <10 | <10 | <10 |
| Shampoo | Mesophilic aerobic germs | <10 | <10 | <10 |
| | Yeasts | <10 | <10 | <10 |
| | Moulds | <10 | <10 | <10 |

These results give evidence of the bacteriostatic and fungistatic effect of the extract of the invention included in the cosmetic compositions given as an example, and show that this effect is maintained in time, the stabilization of the extract being sufficient (1 month at 45° C. corresponds to 1 year's natural ageing). It is to be noted that, without the extract, the number of colonies would have been in the region of 600000 even 500000 depending upon germ type.

In the examples just described, the extract of the invention was used as a technical ingredient of a cosmetic composition in order to protect the latter against risks of microbial contamination and to limit, even omit, the use of chemical preservatives.

However, other forms of use of the extract of the invention may be considered. For example, the algae extract of the invention may be incorporated, in concentrate form, in a cosmetic and/or pharmaceutical composition not only to protect such composition against the risks of microbial contamination, but also as an active product. Depending on its concentration in the cosmetic composition, the extract of the invention may act in selective manner against certain bacteria or certain fungi responsible for unpleasant phenomena such as the onset of dandruff or of acne in adolescents for example.

Tests were conducted with a concentrate of algae extract of the invention on different bacterial strains or yeasts in order to assess its fungicidal and bactericidal action. During these tests, a bacterial strain or yeast was placed in contact with a solution containing the extract concentrate for exactly 30 minutes and 60 minutes. After this contact, 1 ml and 0.1 ml samples of a mother solution containing the concentrate to be tested and the microbial strain were embedded in a PCA medium. The results of these tests are given in the table below in which, for each microbial strain, the population was measured after a contact time of 30 minutes and 60 minutes with a concentration of extract concentrate varying by a factor of 10.

| | Contact time | mother solution | 0.1 ml | 1 ml |
|---|---|---|---|---|
| *Pityrosporum ovale* | 30 min | 8.8 $10^6$/ml | 2.8 $10^4$/ml | 0 |
| | 60 min | 8.8 $10^6$/ml | 2.6 $10^4$/ml | 0 |
| *Staphylococcus aureus* | 30 min | 1.9 $10^8$/ml | $2.10^3$/ml | 0 |
| | 60 min | 1.9 $10^8$/ml | $2.10^3$/ml | 0 |
| *Staphylococcus epidermidis* | 30 min | 2.5 $10^8$/ml | | 0 |

The *Pityrosporum ovale* yeast is one of the major microbial causes for the onset and development of dandruff.

A perfect population decrease (6 Log) is observed in the 1 ml embedding, irrespective of contact time. This population decrease is greater than the 5 Log reduction required by standards in force. Consequently, in a 1 ml culture, the extract concentrate of the invention has fungicidal action against the Pityrosporum ovale yeast.

On the other hand, with a 0.1 ml embedding, that is to say with a dilution by a factor of 10 of the concentrate of clarified algae extract of the invention, the action of this extract is more restricted (with a population decrease of 2 Log) and is of fungistatic type.

This result proves that the extract of the invention can, at certain concentrations, destroy or inhibit the development of the *Pityrosporum ovale* yeast. This extract can therefore be used for its fungicidal action in hair treatment products to destroy dandruff and for its fungistatic action in hair care products to prevent dandruff invasion.

The aerobic bacterial strains *Staphylococcus aureus* and *Staphlyococcus epidermidis*, associated with the Pityrosporum ovale yeast and the anaerobic bacterial strains *Propionibacterium acne* and *Propionibacterium granulosum* are the main microbial causes of skin problems in young persons, especially acne problems.

In respect of the *Staphylococcus aureus* and *Staphylococcus epidermis* strains, a perfect population decrease was also observed (8 Log) with a 1 ml embedding after a contact time of 30 minutes. Also, a 0.1 ml embedding of the *Staphylococcus aureus* strain, that is to say with a factor 10 dilution of the concentrate of algae extract tested, the fungicidal activity of this extract was still evidenced on this strain since a population decrease of 5 Log was observed, which corresponds to the minimum requirement by standards in force.

Having regard to the study of the action of a concentrate of the extract of the invention on the anaerobic bacterial strain *Propionibacterium acnes*, tests were conducted following a different protocol. In this case, the bacterial strain is grown in an anaerobic medium on a M20 liquid medium for 7 days at 25° C. The strain is then inoculated into an aerobic medium. The population of a test strain placed in contact with a concentrate of the extract of the invention for a period of 24 hours, is then compared with the population of a control strain that was not placed in contact with this concentrate. The results of this test are reported in the table below.

| Proprionibacterium acnes | Mother solution | Contact time 24 hours |
|---|---|---|
| Control | $8.10^8$ | $6.10^5$ |
| Test | $6.10^8$ | $5.10^1$ |

These results provide evidence that the concentrate of the extract of the invention has a bactericidal effect on the strain

*Propionibacterium acnes* (a population decrease of 7 Log is observed) when the contact time is relatively long, that is to say at least 24 hours. The fact that the bactericidal action is found after a relatively long contact time, means that, in this case, the halogenated active substances of the extract are released progressively. The bactericidal effect of the concentrate of the extract is therefore proven on *Proprionibacterium acnes*, after a relatively long contact time, but it is less marked than on *Staphylococcus aureus, Staphlyococcus epidemis* and *Pityrosporum ovale*.

On the other hand, up until now, the algae extract of the invention does not seem to have developed any bactericidal action against the fifth bacterial strain attributed to the onset of acne, namely the anaerobic bacterial strain *Propionibacterium granulosum*.

Consequently, a concentrate of the extract of the invention, at certain concentrations, has bactericidal and bacteriostatic action on four of the five microbial strains usually involved in skin problems of the young, particularly acne problems.

On the basis of these results, use of the extract of the invention as an active product in a cosmetic composition and even a pharmaceutical composition can be considered.

The cosmetic and pharmaceutical compositions given below as examples will give a better understanding of the diversity of the formulations in which a concentrate of the extract of the invention may be incorporated as an active substance. In these examples, the trade names of the products used are, whenever applicable, given in brackets, the quantities of product being expressed as a weight %.

Example 4
Anti-acne Cream

|  | Prevention | Treatment |
| --- | --- | --- |
| Water | 53.65 | 48.65 |
| Propylene glycol | 15.00 | 15.00 |
| PEG-8 (Lutrol E 400) | 5.00 | 5.00 |
| Tetrasodium EDTA (powder Edeta B) | 0.05 | 0.05 |
| Triethanol mine | 0.20 | 0.20 |
| Stearic acid | 3.00 | 3.00 |
| Hydrogenated coconut oil | 2.00 | 2.00 |
| Polysorbate 60 | 1.80 | 1.80 |
| Sorbitan stearate | 1.20 | 1.20 |
| Pure wheatgerm oil | 0.50 | 0.50 |
| PEG-100 stearate and lyceryl stearate | 1.30 | 1.30 |
| Vaseline oil | 10.50 | 10.50 |
| DL α tocopherol | 0.50 | 0.50 |
| Concentrate of the extract of the invention | 5.00 | 10.0 |

Example 5
Anti-acne Lotion

|  | Prevention | Treatment |
| --- | --- | --- |
| Water | 65.95 | 60.95 |
| Tetrasodium EDTA (powder Edeta B) | 0.05 | 0.05 |
| Citric acid | 0.05 | 0.05 |
| Xanthane gum | 0.30 | 0.30 |
| Ceteareth-25 (cremophor A25) | 2.00 | 2.00 |
| Steareth-7 (Lamecreme SA7) | 5.00 | 5.00 |
| Glycerine stearate SE | 3.00 | 3.00 |
| Ispropyl myristate | 11.80 | 11.80 |
| Lanolin (Stellux AI) | 1.00 | 1.00 |
| Squalane (Cosbiol) | 5.00 | 5.00 |
| DL α tocopherol | 0.50 | 0.50 |
| Concentrate of the extract of the invention | 5.00 | 10.00 |
| Fragrance (Acacia 887) | 0.35 | 0.35 |

Example 6
Anti-acne Gel

|  | Prevention | Treatment |
| --- | --- | --- |
| Water | 87.20 | 82.20 |
| Carbomer (polmer LL) | 0.40 | 0.40 |
| PEG-8 (Lutrol E400) | 2.00 | 2.00 |
| Propylene glycol | 5.00 | 5.00 |
| Triethanolamine | 0.40 | 0.40 |
| Concentrate of the extract of the invention | 5.00 | 10.00 |

Example 7
Anti-dandruff Astringent Gel

|  | Prevention | Treatment |
| --- | --- | --- |
| Water | 92.00 | 87.00 |
| Carragheens (Carraghenate X2) | 3.00 | 3.00 |
| Concentrate of the extract of the invention | 5.00 | 10.00 |

Example 8
Anti-dandruff Lotion

|  | Prevention | Treatment |
| --- | --- | --- |
| Water | 57.90 | 52.90 |
| Hydrogenated castor oil PEG-40 | 0.50 | 0.50 |
| Fragrance | 0.30 | 0.30 |
| Ethanol | 30.00 | 30.00 |
| Panthenol | 0.50 | 0.50 |
| Concentrate of the extract of the invention | 5.00 | 10.00 |

Example 9
Anti-dandruff Shampoo

|  | Prevention | Treatment |
| --- | --- | --- |
| Water | 60.65 | 55.65 |
| Sodium laureth sulphate | 25.00 | 25.00 |
| Linoleamide DEA | 2.00 | 2.00 |
| Hydrolysed collagen of | 1.50 | 1.50 |

-continued

|  | Prevention | Treatment |
|---|---|---|
| potassium cocoyl cocoamidopropylbetaine | 3.00 | 3.00 |
| Tetrasodium EDTA | 0.20 | 0.20 |
| Citric acid | 0.15 | 0.15 |
| Sodium chloride | 2.50 | 2.50 |
| Concentrate of the extract of the invention | 5.00 | 10.00 |

In all these formulations, no preservative was added since the concentrate of the extract of the invention is used not only as an active substance but also for the self-protective role it confers upon the composition against microbial contamination.

Evidently, it is possible to obtain derivatives of the extract by modifying its physicochemical qualities or its concentration. Said derivatives, having antibacterial or antifungal activity, remain within the scope of the claimed object of the invention.

What is claimed is:

1. A method of obtaining from algae a clarified composition having antibacterial and/or antifungal activity, wherein said algae comprises polysaccharide, intracellular components and intravesicular components, said method comprising:

(A) maturing an algae mixture comprising burst algae cells at a maximum temperature of 4° C. for a period of time sufficient to result in natural enzymatic degradation of the polysaccharides in the algae mixture, but a time insufficient to result in loss of antibacterial and/or antifungal activity in the algae mixture;

(B) releasing the intracellular component and intravesicular components of the algae mixture;

(C) centrifuging the algae mixture of Step (B) at a speed sufficient to collect a supernatant containing algae components having antibacterial and/or antifungal properties; and (D) clarifying the supernatant of Step (C) by microfiltration to obtain a clarified composition having halogenated organic molecules having a molecular weight of more than 10,000, said composition having antibacterial and/or antifungal activity and wherein said algae are Bonnemaisoniacea.

2. The method of claim 1, wherein the algae are *Asparagopsis armata*.

3. The method of claim 1, further comprising adding $H_2O$ to the mature algae mixture in Step (A), to produce a mature algae mixture in which the quantity of organic matter is 8% or less by weight.

4. The method of claim 1, wherein the supernatant of step (C) is acidified with citric acid.

5. The method of claim 1, wherein the supernatant of step (C) is acidified to a pH between about 2 and 5.

6. The method of claim 1, wherein the supernatant of step (C) is acidified to pH 3.35.

7. The method of claim 1, wherein the filtration of step (D) is tangential microfiltration.

* * * * *